(12) United States Patent
Seeram et al.

(10) Patent No.: US 10,155,738 B2
(45) Date of Patent: Dec. 18, 2018

(54) METHODS FOR SKIN WHITENING USING A GALLOTANNIN

(71) Applicant: RHODE ISLAND BOARD OF EDUCATION, STATE OF RHODE ISLAND & PROVIDENCE PLANTATIONS, Providence, RI (US)

(72) Inventors: Navindra Seeram, Charlestown, RI (US); Hang Ma, Kingston, RI (US); Keykavous Parang, Irvine, CA (US)

(73) Assignee: University of Rhode Island, Kingston, RI (US)

( * ) Notice: Subject to any disclaimer, the term of this patent is extended or adjusted under 35 U.S.C. 154(b) by 0 days.

(21) Appl. No.: 15/301,605

(22) PCT Filed: Apr. 6, 2015

(86) PCT No.: PCT/US2015/024506
§ 371 (c)(1),
(2) Date: Oct. 3, 2016

(87) PCT Pub. No.: WO2015/154074
PCT Pub. Date: Oct. 8, 2015

(65) Prior Publication Data
US 2017/0029397 A1    Feb. 2, 2017

Related U.S. Application Data

(60) Provisional application No. 61/975,668, filed on Apr. 4, 2014.

(51) Int. Cl.
C07D 309/10    (2006.01)
(52) U.S. Cl.
CPC ................. *C07D 309/10* (2013.01)
(58) Field of Classification Search
CPC .................................................. C07D 309/10
USPC ........................................................ 549/417
See application file for complete search history.

(56) References Cited

U.S. PATENT DOCUMENTS

2003/0078212 A1    4/2003    Li et al.
2013/0310332 A1    11/2013    Barbeau et al.

FOREIGN PATENT DOCUMENTS

KR       20120079983       *    7/2012
WO       WO 2012055010     *    5/2012

OTHER PUBLICATIONS

Yuan; Tetrahedron 2012, 68, 959-964.*
Honma; Food Chemistry 2010,123, 390-394.*
Wan; Bioorganic & Medicinal Chemistry Letters 2012, 22, 597-600.*
Khanbabaee; Nat. Prod. Rep., 2001, 18, 641-649.*
Ma; RSC Adv., 2015, 5, 107904-107915.*
Zhao; Journal of Chromatography B, 2007, 850, 523-527.*
Chen et al, "Melanogenesis Inhibition by Gallotannins from Chinese Galls in B16 Mouse Melanoma Cells," Biol. Pharm. Bull., vol. 32, pp. 1447-1452, (2009), (6 pages).
Ren et al, "Synthesis and Structure-Activity Relationship Study of Antidiabetic Penta-O-galloyl-D-glucopyranose and Its Analogues," J. Med. Chem., vol. 49, pp. 2829-2837, (2006), (9 pages).
International Search Report and Written Opinion issued by the International Searching Authority in International Application No. PCT/US15/24506,

* cited by examiner

*Primary Examiner* — Daniel R Carcanague
(74) *Attorney, Agent, or Firm* — Davis, Brown, Koehn, Shors & Roberts, P.C.; Sean D. Solberg

(57) ABSTRACT

A method is disclosed for synthesizing a compound that includes gallotannins from a part of a maple tree, into new skin whitening compounds. The method includes the step of isolating the gallotannin from the part of the maple tree.

3 Claims, 10 Drawing Sheets

METHODS FOR SKIN WHITENING USING A GALLOTANNIN

PRIORITY

The present application claims priority to International Patent Application No. PCT/US2015/024506 filed Apr. 6, 2015, which claims priority to U.S. Provisional Patent Application Ser. No. 61/975,668 filed Apr. 4, 2014, both of which are incorporated herein by reference in their entireties.

BACKGROUND

The biosynthesis of melanin is collectively regulated by over 100 distinct genes. In mammals, three enzymes, tyrosinase (TYR), tryosinase-related protein-1 (TRP-1) and tryosinase-related protein-2 (TRP-2) are essential for the overall melanin production. Tyrosinase performs a pivotal role in the modulation of melanogenesis. It is the rate-limiting enzyme that catalyzes the hydroxylation of L-tyrosine into 3,4-dehydroxyphenylalanine (DOPA) and consequently oxidizes DOPA into DOPA quinone. TRP-2, which serves as a DOPA-chrome tautomerase (DCT), further promptly coverts DOPA quinone into 5,6-dihydroxyindol-2-carboxylic acid (DHICA), whereas TRP-1 facilitates the oxidization of DHICA to form carboxylated indole-quinone. Two types of melanin are produced: a red/yellow pheomelanin and a black/brown eumelanin. The TYR enzyme is critically involved in both pheomelanin and eumelanin synthesis while TRP-1 and DCT contribute more in the synthesis of eumelanin. Microphthalmia-associated transcription factor (MITF) is a primary transcriptional activator of the melanogenic enzymes and seems to be the principle transcription regulator that mediates the survival, proliferation and differentiation of melanoblasts and melanocytes. Given that melanin synthesis in mammal involves multiple-step catalyzation that modulated by a group of enzymes and transcription factors, it is important to understand the biological molecular mechanisms of melanogenesis inhibitors.

In mammals, skin pigments are produced in the melanosomes of melanocytes cells that are situated on the basal layer between the dermis and epidermis. The pigmentation plays a crucial role in terms of protecting skin against radiation-induced damage such as exposure to ultraviolet light. However, overproduction or abnormal accumulation of melanin may lead to many skin hyperpigmentation disorders including freckles, age spots, post-inflammatory hyperpigmentation and even melanoma. Undesired excessive skin pigmentation is a severe health concern since it can cause negative burdens on patients' psychological well-being. Thus, skin depigmentation remains a compelling research area for the cosmetic industry and the exploration of novel classes of safe and effective melanogenesis inhibitors from natural sources has attracted immense research interest.

There remains a need, therefore, for improved skin whitening compounds with enhanced skin whitening capabilities.

SUMMARY

In an embodiment, the invention provides a method for synthesizing a compound that includes gallotannins from a part of a maple tree, into new skin whitening compounds. The method includes the step of isolating the gallotannin from the part of the maple tree.

In certain embodiments, the skin whitening compound is tetragalloylglucitol. In further embodiments, the skin whitening compound includes the following:

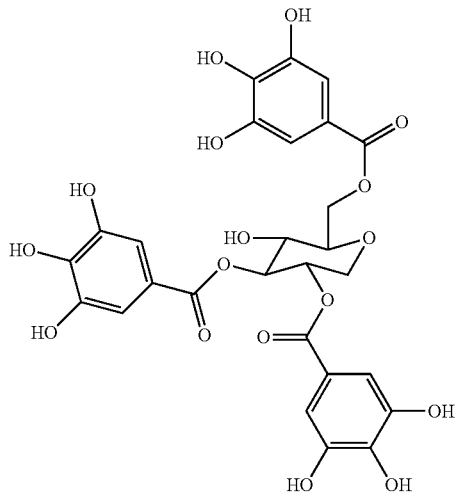 [SMILES: O=C(OCC1OCC(OC(=O)c2cc(O)c(O)c(O)c2)C(OC(=O)c2cc(O)c(O)c(O)c2)C1O)c1cc(O)c(O)c(O)c1]

In further embodiments, the skin whitening compound includes the following:

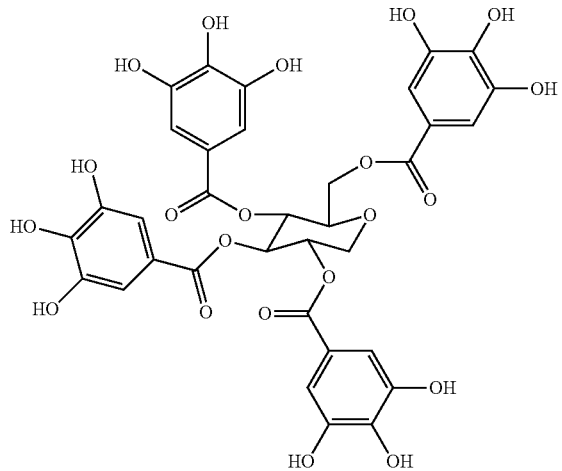 [SMILES: O=C(OCC1OCC(OC(=O)c2cc(O)c(O)c(O)c2)C(OC(=O)c2cc(O)c(O)c(O)c2)C1OC(=O)c1cc(O)c(O)c(O)c1)c1cc(O)c(O)c(O)c1]

BRIEF DESCRIPTION OF THE DRAWINGS

The following description may be further understood with reference to the accompanying drawings in which.

DETAILED DESCRIPTION

The mechanism of the inhibitory effects of ginnalinginnalins A-C on melanogenesis in B16F10 cells were elucidated by using real-time PCR and Western blot experiments. The results indicated that ginnalinginnalins were able to down-regulate the expression of MITF, TYR, TRP-1 and TRP-2 gene levels in a time and dose-dependent manner and significantly reduce the protein expression of TRP-2 gene. The findings indicate that phytochemicals in red maple leaves possess anti-melanogenic effects and thus may have cosmetic skin-whitening application.

The maple genus (*Acer*) comprises of over 120 species, most of which are found in Asia, with the remaining being native and endemic to North America. Phytochemical and biological investigation of *Acer* species including *A. buergerianum* (China maple) and *A. nikoense* (Japanese maple) resulted in a number of compounds with anti-melanogenic effects in B16F10 cells. Interestingly, *A. rubrum* L. (red maple) which is native to eastern North America was traditionally used as a folk medicine by the Native Americans for many ailments including dermatological disorders.

Figure 1:
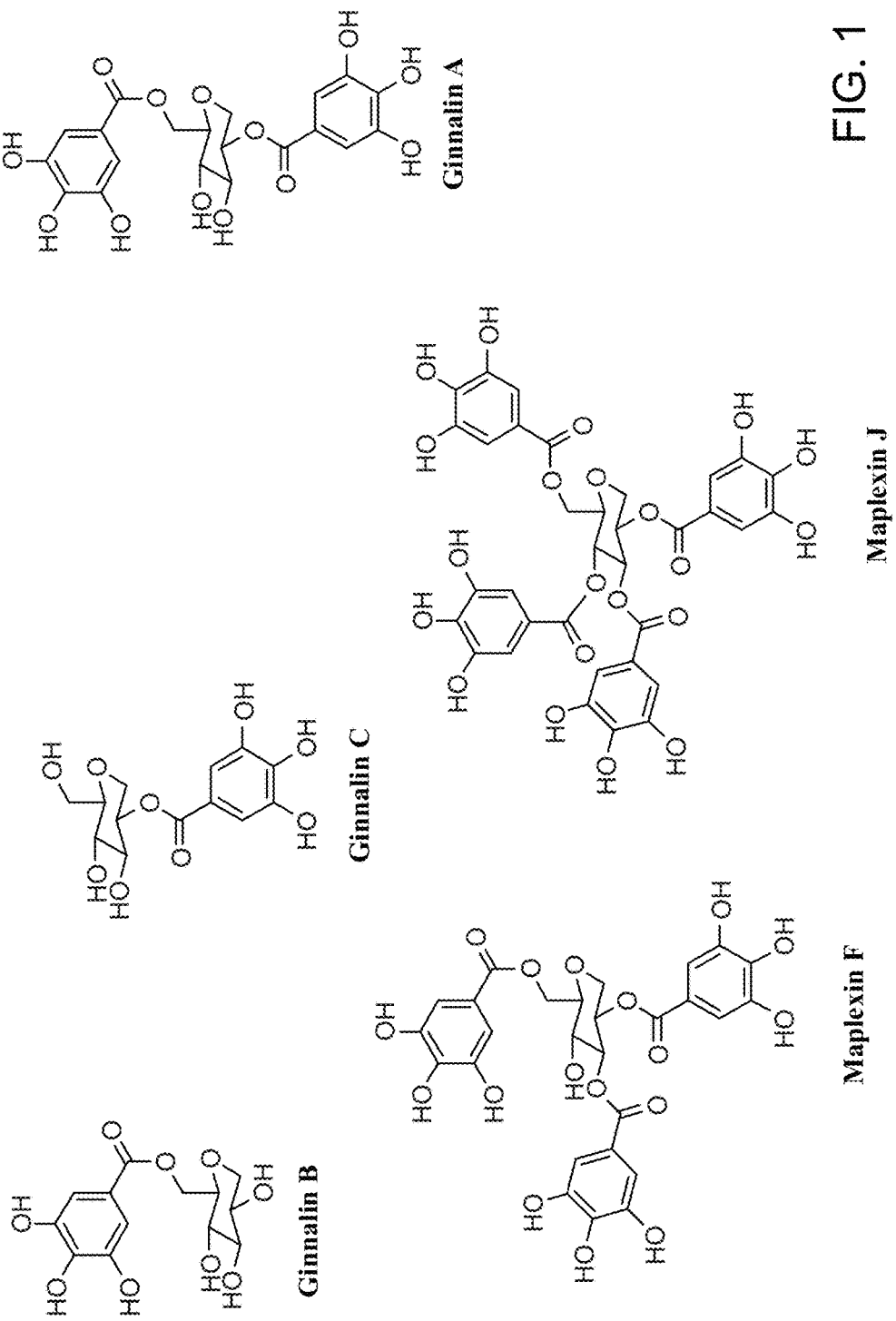
FIG. 1 shows illustrative views of chemical structures of ginnalinginnalins A-C (1-3) and maplexins F (4) and J (5)

The chemical structures of maple gallotannins: ginnalins A-C and maplexins F and J are shown in FIG. 1. Although many synthetic compounds, such as hydroquinone and its derivatives had been conventionally used to suppress the over production of melanin, their application in cosmetics have been restrained because of the lack of effectiveness or potential side effects including skin irritation and/or toxicity. Therefore, natural products and botanical extracts have emerged as attractive candidates for melanogenesis inhibitory applications since they tend to be safe and have fewer adverse effects than synthetic compounds.

A series of bioactive gallotannins were isolated from a part of a maple tree. These gallotannins reside in maple trees that include red maple, sugar maple, silver maple, sycamore maple, Norway maple, and black maple. In this embodiment, the gallotannins were isolated from the leaves of the red maple (*Acer rubrum*) species, namely ginnalinginnalins A-C and the new molecules named maplexins A-I, with potent antioxidant capacities. Other embodiment include gallotannins isolated from the extracts of maple twigs, stems, and bark. These natural compounds contain 1, 2 or 3 galloyl groups (from a possible 4 locations) attached to a 1,5-anhydro-D-glucitol moiety.

This embodiment shows the cosmetic skin lightening/whitening applications of a novel extract from the leaves of the red maple species, Maplifa, in enzyme and cell based assays. Maplifa contains ca. 45-50% of ginnalinginnalin A along with other gallotannins including ginnalinginnalins B and C and maplexins. SAR studies showed that increasing the number of galloyl groups attached to the 1,5-anhydro-D-glucitol moiety resulted in greater inhibitory effects on tyrosinase enzyme. Consequently, maplexin J, the first tetra-galloyl-glucitol (contains the maximum number of 4 galloyl groups) was synthesized, and confirmed the SAR observations. Purified Ginnalinginnalins A-C, as the representative gallotannins in Maplifa, were assayed for their inhibitory effects on melanin production in B16F10 cells. GinnalinGinnalin A (contains 2 galloyl groups) clearly reduced the melanin content at 50 µM whereas ginnalinginnalin B and C (contains 1 galloyl group each) showed only minor anti-melanogenic effects.

Another embodiment taught the synthesis of maplexin J, which is the first tetragalloyl substituted glucitol reported to date. Maplexin J was 80-fold more potent (2 vs. 160 M) than acarbose, a clinical α-glucosidase inhibitor drug. Maplexin J was the most active α-glucosidase inhibitor among all maplexins reported so far.

Example 1. Effects of Ginnalinginnalins A-C and Maplifa on Tyrosinase Activity

Inhibitory effects of Maplifa, an ginnalins-riched fraction from the leaves of red maple, along with five phenolic compounds, ginnalinginnalins A-C (1-3) and maplexin F and J (4-5), on mushroom tyrosinase activity were assayed and their $IC_{50}$ values are shown in Table 1. Maplifa was prepared by new methods developed in the laboratory. Briefly, leaves of red maple were dried and macerated in aqueous ethanol to obtain the crude extract which was then further purified on a resin column to remove chlorophyll and other plant pigments. Maplifa was obtained as an off-white free flowing powder after solvent removal.

The major gallotannins in Maplifa were identified by comparison of high performance liquid chromatography (HPLC) profiles of Maplifa and authentic gallotannin standards previously isolated by our group. A stock solution of 1 mg/mL of Ginnalinginnalin A was prepared in DMSO and then serially diluted to afford samples of 0.5, 0.25, 0.125, 0.0625, 0.03125 mg/mL concentrations, respectively. Each sample was injected in triplicate and a linear six-point calibration curve ($r^2$=0.9997) was constructed by plotting the mean peak area percentage against concentration. Maplifa samples were prepared at stock solutions of 2.2 mg/mL in DMSO. All HPLC-UV analyses were carried out with 20 µL injection volumes on a Luna C18 column and monitored at a wavelength of 280 nm. A gradient solvent system consisting of solvent A (0.1% aqueous tri-fluoro-acetic acid) and solvent B (methanol, MeOH) was used with a flow rate at 0.75 mL/min as follows: 0-30 min, 10%-60% B; 30-35 min, 60%-100% B; 35-40 min, 100% B; 40-41 min, 100%-10% B; 41-51 min, 100% B. The concentration of ginnalinginnalins A-C in the maple extracts was quantified based on the standard curves.

Figure 2:
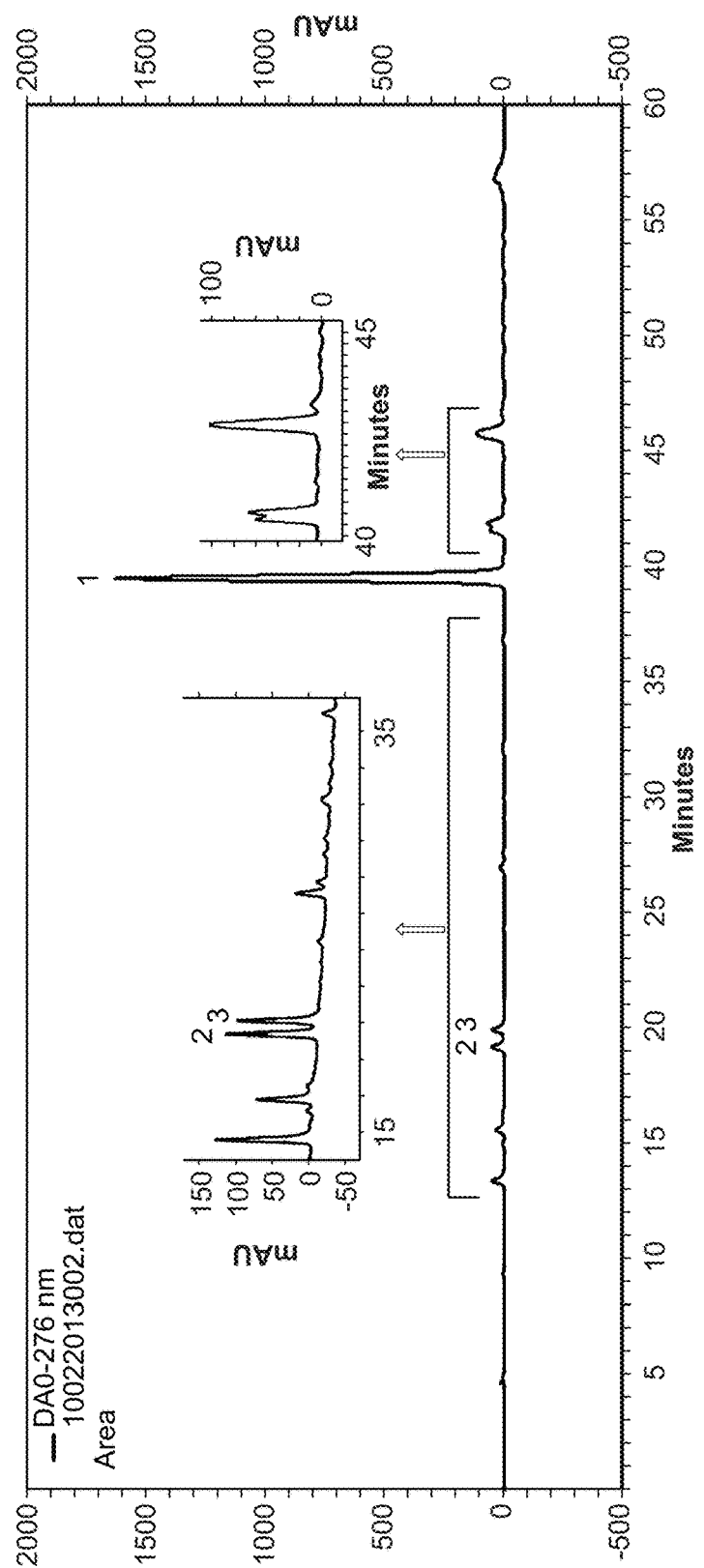
FIG. 2 shows an illustrative graphical representation of HPLC-UV chromatograms of Maplifa.

HPLC-UV chromatograms of Maplifa™, an ginnalin A-riched extract, showing the presence of ginnalins A-C (1-3) in the Maplifa™ extract are shown in FIG. 2.

The chemical structures of ginnalinginnalins and maplexins are shown in FIG. 1. It was found that gallotannins with two to four galloyl groups were more active than acertanins with only one galloyl group. GinnalinGinnalin A (1), a 1,5-anhydro-D-glucitol moiety with two galloyl groups, showed high inhibitory activity with an $IC_{50}$ value of 181.9 µM. Similarly, maplexin F (4) and maplexin J (5), with three or four galloyl groups respectively, showed comparable $IC_{50}$ values of 212.2 and 190.4 µM. However, gallotannins with only one galloyl group, namely, ginnalinginnalin B (2) and ginnalinginnalin C (3), only showed weak inhibitory effects ($IC_{50}$=1047.3 and 857.8 µM, respectively) on the tyrosinase enzyme.

TABLE 1

Table 1: Tyrosinase Enzyme Inhibition Assay. Inhibitory activity ($IC_{50}$) of an ginnalin-riched extract (Maplifa) and five phenolics, ginnalinginnalins A-C (1-3), and maplexins F-J (4-5).

| Compound | # of galloyl group | $IC_{50}^{a}$ |
|---|---|---|
| Ginnalin A | 2 | 181.9 ± 3.5 |
| Ginnalin B | 1 | 1047.3 ± 2.7 |
| Ginnalin C | 1 | 857.8 ± 6.9 |
| Maplexin F | 3 | 212.2 ± 5.5 |
| Maplexin J | 4 | 190.4 ± 1.7 |
| Maplifa | — | 154.5 ± 5.4 |
| Kojic acid* | — | 21.4 ± 0.1 |
| Arbutin* | — | 63.0 ± 0.3 |

$^{a}IC_{50}$ are presented in concentration of μM for pure compounds and ppm for Maplifa. Each value is presented as mean ± S.D. from triplicate independent experiments.
*Positive controls.

Table 1 shows Inhibitory activity (IC50) of five phenolics, ginnalins A-C and maplexins F-J, on tyrosinase enzyme. aIC50 are presented as mean±S.D. from triplicate independent experiments. *Positive controls.

Example 2: Cell Viability of Maplifa and Ginnalinginnalins A-C on B16F10 Cells To further investigate the anti-melanogenic activities of ginnalinginnalins A-C, present in the Maplifa extract, cellular based assay were employed to measure the melanin content on murine melanoma B16F10 cells. In order to determine the non-toxic concentrations of ginnalinginnalins for cellular assays, cell viability on B16F10 cells were first evaluated by using MTS assay. The MTS assay was carried out as described previously with modifications. At the end of either 24, 48 or 72 h of treatment with test samples (in the concentration range of 1-100 μM for purified gallotannins and 6.25-200 μg/mL for Maplifa extract), 20 μL of the MTS reagent, in combination with the electron coupling agent, phenazine menthosulfate, were added to the wells and cells were incubated at 37° C. in a humidified incubator for 3 h. Absorbance at 490 nm was monitored with a spectrophotometer (SpectraMax M2, Molecular Devices Corp., operated by SoftmaxPro v.4.6 software, CA, USA) to obtain the number of cells relative to control populations. The inhibition of proliferation in the sample treatment cells were expressed as percentage compared to control (0.1% DMSO) cells. Data was presented as mean values±S.D. and were obtained from three separate experiments. Two-tailed unpaired student's t-test was used for statistical analysis of the data using the Office Excel 2010 software. A p value <0.05 was considered significant.

Murine melanoma B16F10 was purchased from the American Type Culture Collection (Rockville, Md.). Cells were cultured in Dulbecco's Modified Eagle Medium (DMEM) medium (Wilkem Scientific, R.I.) that was supplemented with 10% v/v fetal bovine serum, 1% v/v nonessential amino acids and 1% v/v antibiotic solution at 37° C. in 5% $CO_2$. Samples were dissolved at a concentration of 50 mg/mL in dimethylsulfoxide (DMSO) as stock solution and then diluted to the desired final concentrations with growth medium. The final DMSO concentration was less than 0.1%.

Figure 3A:
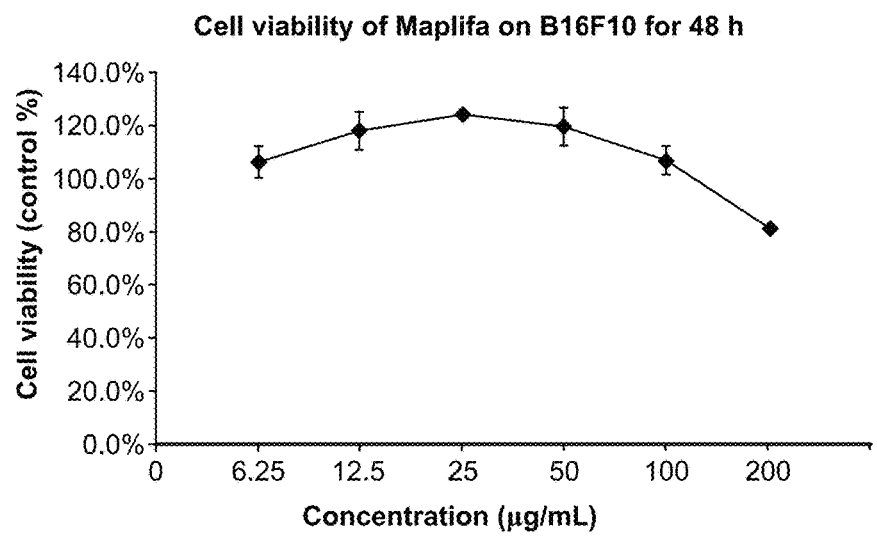
FIGS. 3A and 3B show illustrative graphical representations of cell viability of Maplifa on B16F10 for 48 hours and 72 hours.
Figure 3B:
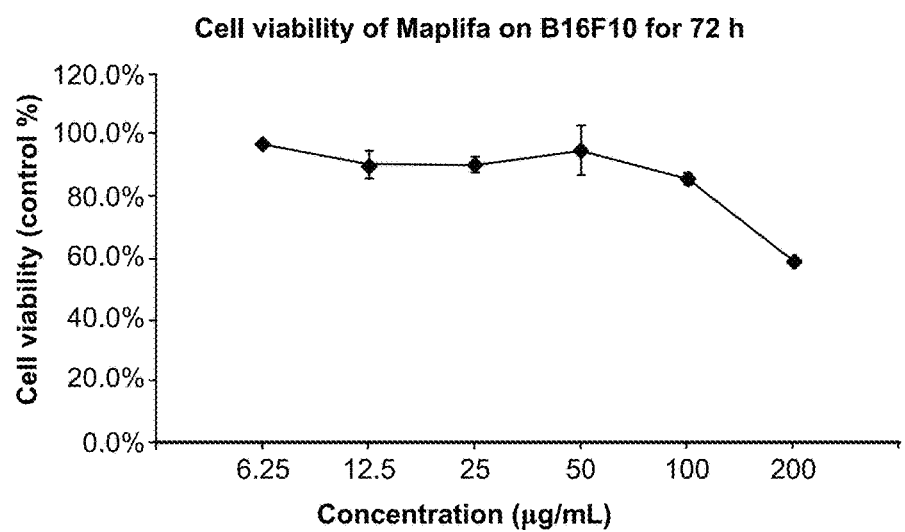

Melanoma B16F10 cells were treated with serial concentrations of Maplifa (6.25, 12.5, 25, 50, 100, and 200 μg/mL) for 48 and 72 h. In addition, various concentrations (0, 5, 10, 25, and 50 μM) of ginnalinginnalins A-C for 72 h and the cell viabilities were determined by comparing with the untreated control group. Each value is presented as mean±S.D. from triplicate independent experiments. FIGS. 3A and 3B, show the effect of Maplifa™ on viability of B16F100 cells for 48 hours and for 72 hours. Maplifa was non-toxic at the concentrations from 6.25 to 100 μg/mL.

Figure 4:
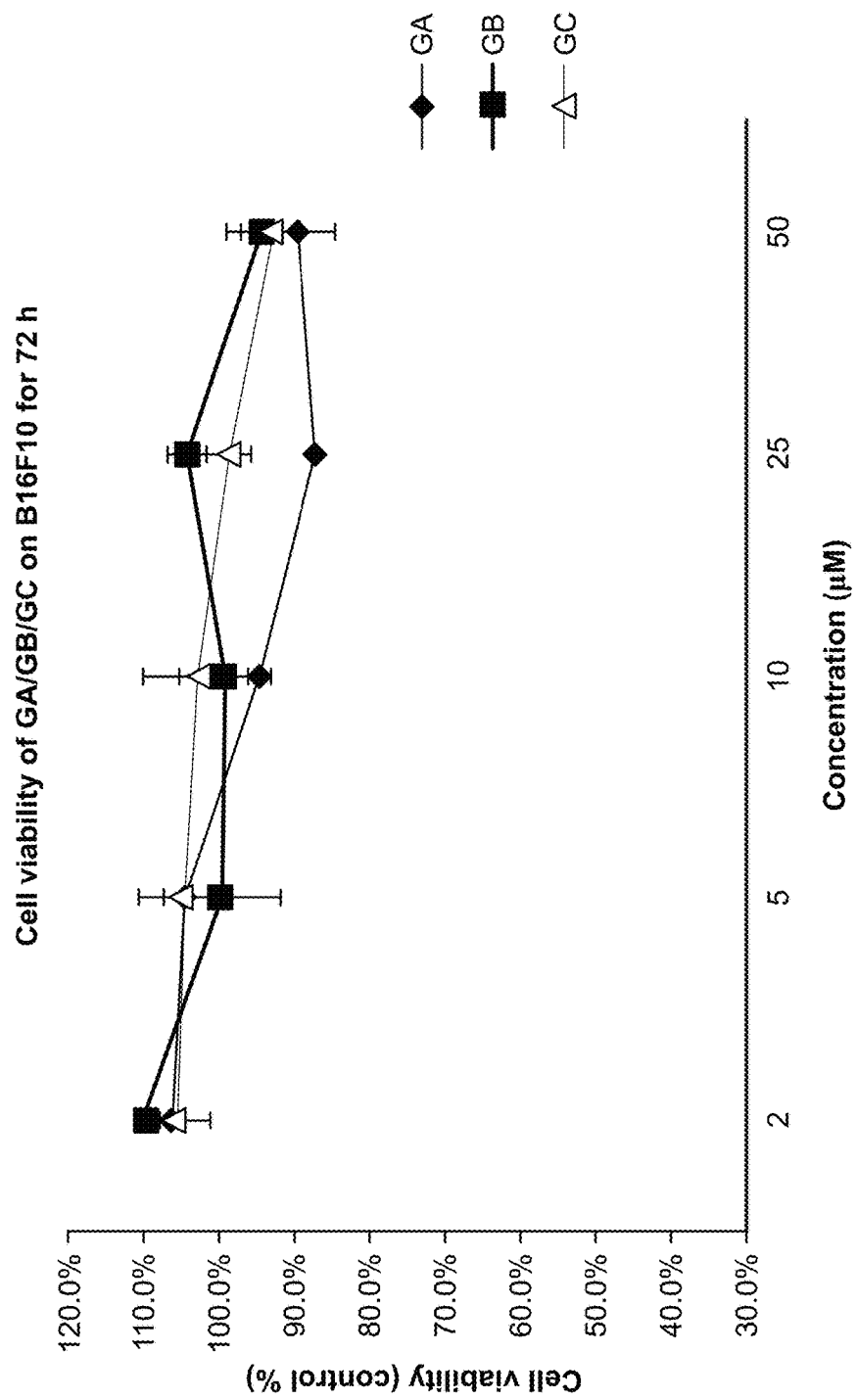
FIG. 4 shows an illustrative graphical representation of the effect of ginnalinginnalins A-C (1-3) on viability of B16F10 cells.

Similarly, in FIG. 4, all of the ginnalinginnalins B and C were found to be non-toxic to B16F10 cells at all concentrations from 0 to 50 μM (cell viabilities >90%), while, ginnalinginnalin A was non-toxic at low concentrations (5 and 10 μM) but slightly reduced the B16F10 cell viabilities to 87.0% and 89.5% at concentrations of 25 and 50 μM, respectively. FIG. 4 shows the effect of ginnalins A-C (1-3) on viability of B16F10 cells. After 72 hours of treatment of serial concentrations (2-50 μM) of ginnalins (1-3), the viability of melanoma B16F10 cells were determined by MTS assay. Each value is presented as mean±S.D. from triplicate independent experiments According to findings from previous studies that screens for safe and effective melanogenesis inhibitors in cell based assays, 40 μg/mL is a threshold concentration for cellular melanogenesis assays. All of the concentrations of the ginnalinginnalins in the study were lower than this published threshold and can be considered as being non-toxic doses resulting in safe melanogenesis inhibitory agents.

Example 3: Effect of Ginnalinginnalins A-C on Melanin Contents

The contents of biosynthesized melanin in melanoma B16F10 cells that treated with ginnalinginnalins A-C at serial concentrations were evaluated by comparing with the control group. The melanin content was determined using a modification of the method described by Liang and Ho. Briefly, B16F10 cells ($5\times10^4$ cells/well) were first seeded in 24-well plates for 24 h and then medium was changed with new DMEM medium containing test samples of various concentrations. After 72 h incubation, the cells were harvested through trypsinization and washed with phosphate-buffered saline (PBS) twice. Then cells were lyzed with 1 N NaOH containing 10% DMSO and heated at 80° C. for 1 h. After samples cooled down to room temperature, the amount of melanin content was spectrophotometrically measured at 400 nm.

Figure 5:
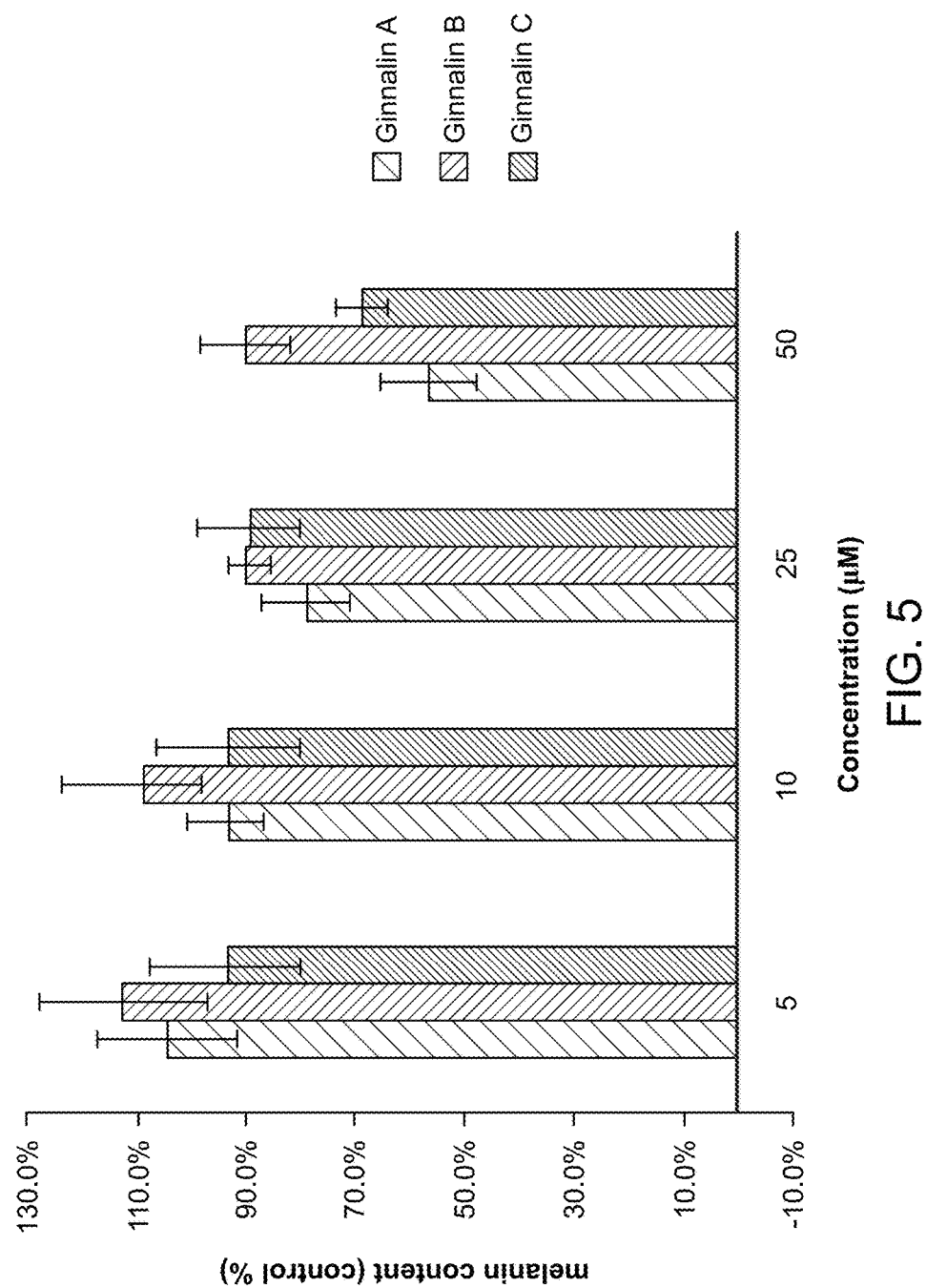
FIG. 5 shows an illustrative graphical representation of the inhibition of melanin synthesis in B16F0 cells by ginnalinginnalins A-C (1-3)

FIG. 5 shows Inhibition of cellular ÿ elanin content in B16F10 cells by ginnalins A-C. Cells were treat with of ginnalins A-C for 72 h, and the melanin content were compared to the control group. Each value is presented as mean±S.D. for triplicate independent experiments. Although in FIG. 5 ginnalinginnalins did not show significant inhibitory activities on melanin biosynthesis at low concentrations (5 and 10 μM), ginnalinginnalin A reduced the formation of melanin at relatively high dosages. The melanin contents in B16F10 that treated with 25 and 50 μM of ginnalin A clearly decreased to 79.1% and 56.7%, respectively, compared to those of in control group, while, ginnalin C slightly reduced melanin level to 89.7% and 68.8% at 25 and 50 μM, respectively. In addition, cells treated with 25 and 50 μM of ginnalin B remained melanin level at 90.0% comparing with the control group.

The effect of ginnalins A-C on tyrosinase-related gene and protein expression was found to be the following. Melanin biosynthesis involves multi-step pathways. In order to determine the molecular mechanisms of inhibitory effects of ginnalins on melanin synthesis, expression levels of melanogenesis related genes, including MITF, TYR, TRP-1 and TRP-2, in B16F10 cells were analyzed by using RT-PCR. The B16F10 cells were planted in 6-well plates at a density of $2.0\times10^5$ cells/well. After being incubated for 24 h, cells were treated with 2 or 10 μM of ginnalins for 48 or 72 h.

Total RNA was isolated from cells using TRIzol reagent (Invitrogen) according to the manufacturer's instructions. One microgram of total RNA was converted to single-stranded cDNA using oligo(dT)18 primers, and mRNA levels were quantified by quantitative real-time PCR using a Roche LightCycler detection system (Roche Applied Science, Mannheim, Germany). Samples were run by using SYBR Green and compared with levels of b2m rRNA as a reference housekeeping gene. Quantitative real-time PCR conditions were optimized for each gene using appropriate forward and reverse primers. The primers used are listed in Supplemental material. All oligonucleotides were synthesized by Invitrogen Inc., CA.

Figure 6A:
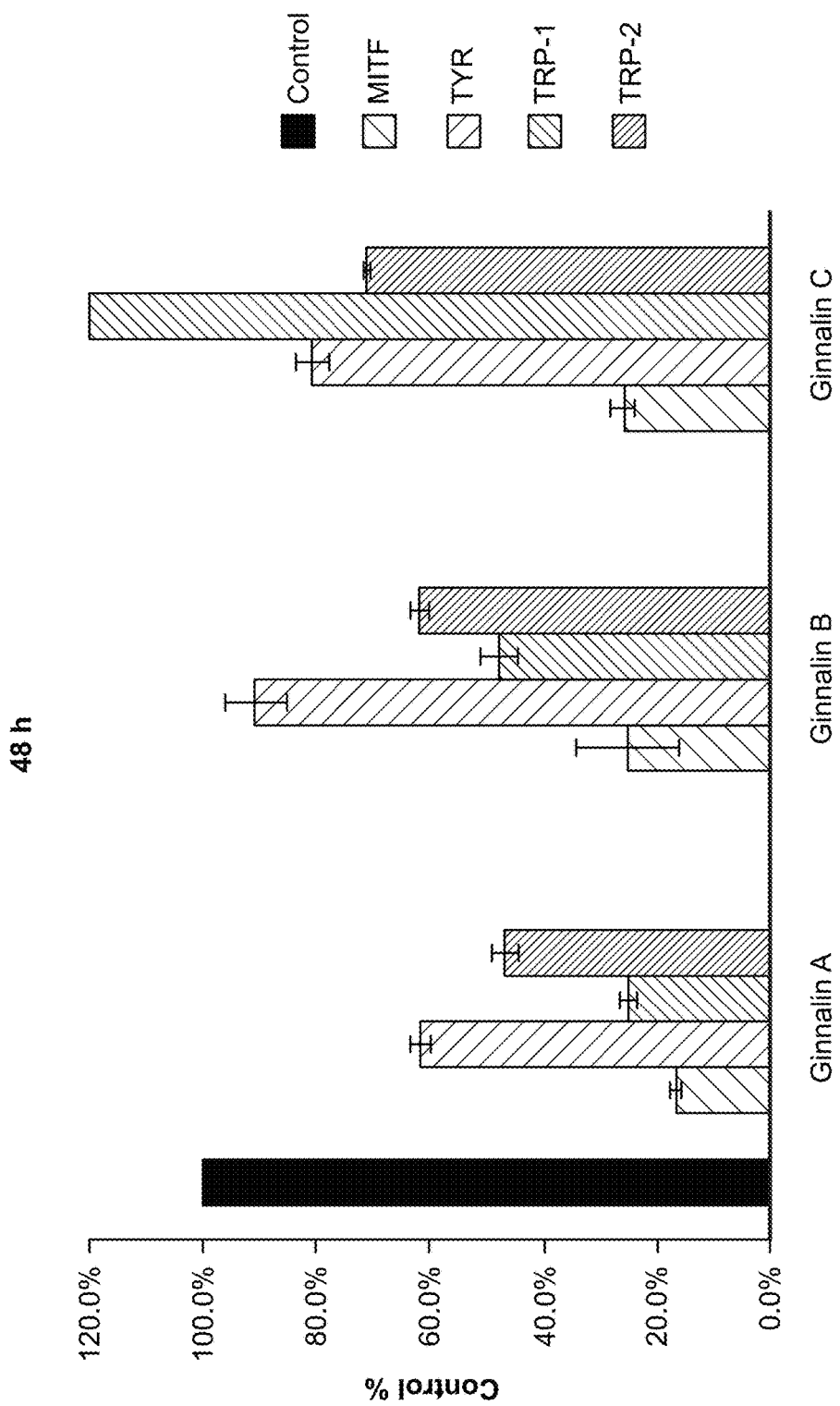
FIGS. 6A and 6B show illustrative graphical representations of the mRNA expression of MITF, TYR, TRP-1 and TRP-2 in ginnalinginnalins treated B16F0 cells.
Figure 6B:
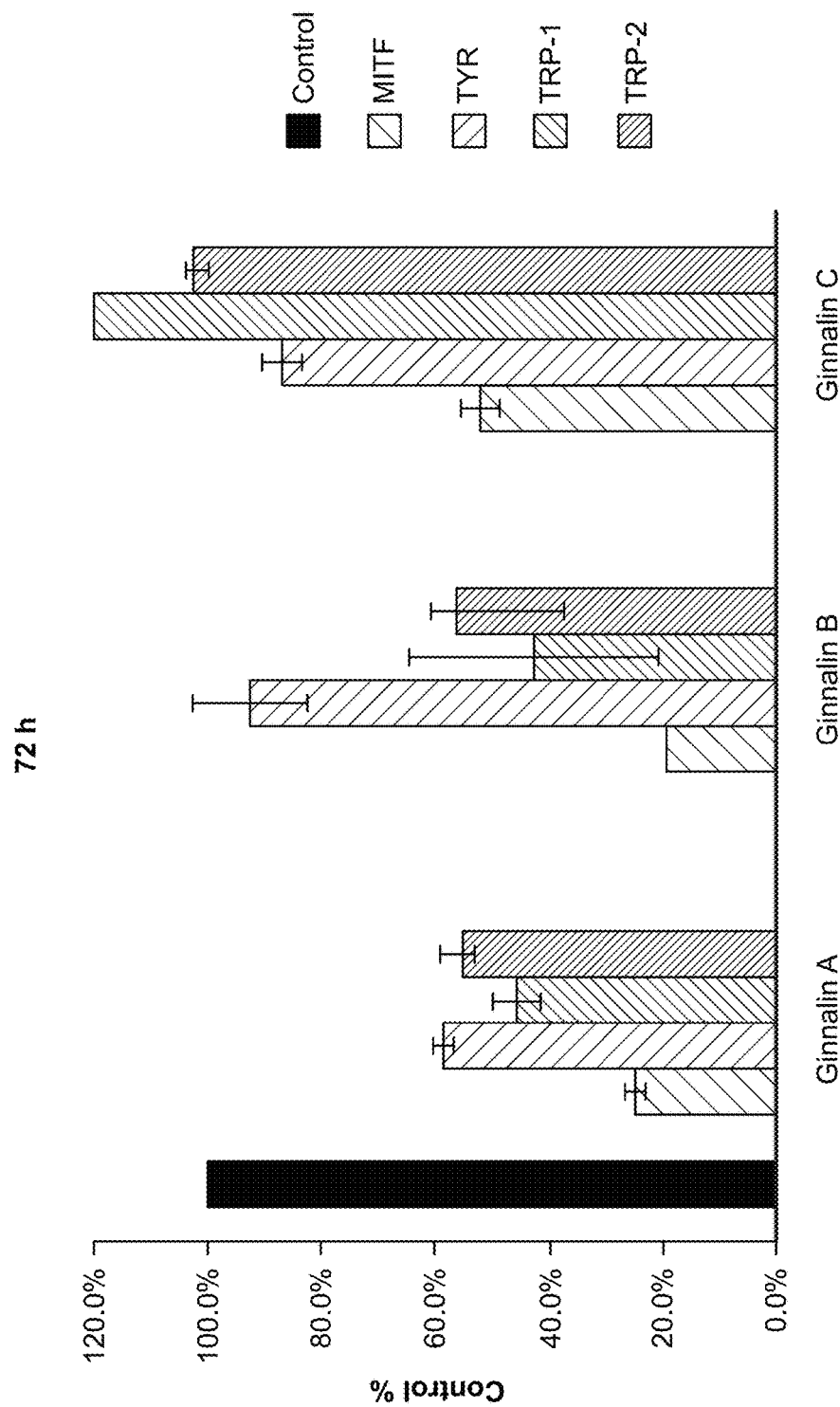

FIGS. 6A and 6B show The mRNA expression of MITF, TYR, TRP-1 and TRP-2 in ginnalins-treated B16F0 cells. Cells were treated with or without 10 µM of ginnalins for 48 hours and 72 hours respectively. As shown in FIGS. 6A and 6B, cells were treated with or without 10 µM of ginnalins for 48 h (A) and 72 h (B). After treated with 10 µM of ginnalin A for 48 h or 72 h, the mRNA expressions of MITF, TYR, TRP-1 and TRP-2 were significantly reduced. Although ginnalin B only slightly decreased the TYR expression by 10.0 and 7.5% at 48 and 72 hours, it significantly decreased the mRNA expressions of MITF, TRP-1 and TRP-2 at 48 and 72 hours. In addition, ginnalin C did not reduce the TRP-1 expression level at all time points and only slightly decreased TYR and TRP-2 expression; however, it significantly down-regulated the mRNA expression of MITF at 48 and 72 hours.

Furthermore, the regulation of ginnalins on the protein expressions of melanogenesis related enzymes in B16F10 cells were evaluated by using Western blot. Expressions of melanin biosynthesis-related proteins, including MITF, TYR, TRP-1 and TRP-2 expression in B16F10 cells were measured by western blot. After incubation with ginnalins for 72 h, proteins from cells were resolved by SDS-PAGE and then transferred to polyvinylidene fluoride membrane. The membrane was blocked with 5% nonfat dry milk in Tris-buffered saline with Tween followed by incubation with primary antibodies overnight. Bands were visualized on X-ray film using an ECL detection kit (Amersham Biosciences, Piscataway, N.J.). A list of antibody, source, and dilution is listed in Supplementary material.

Figure 7:
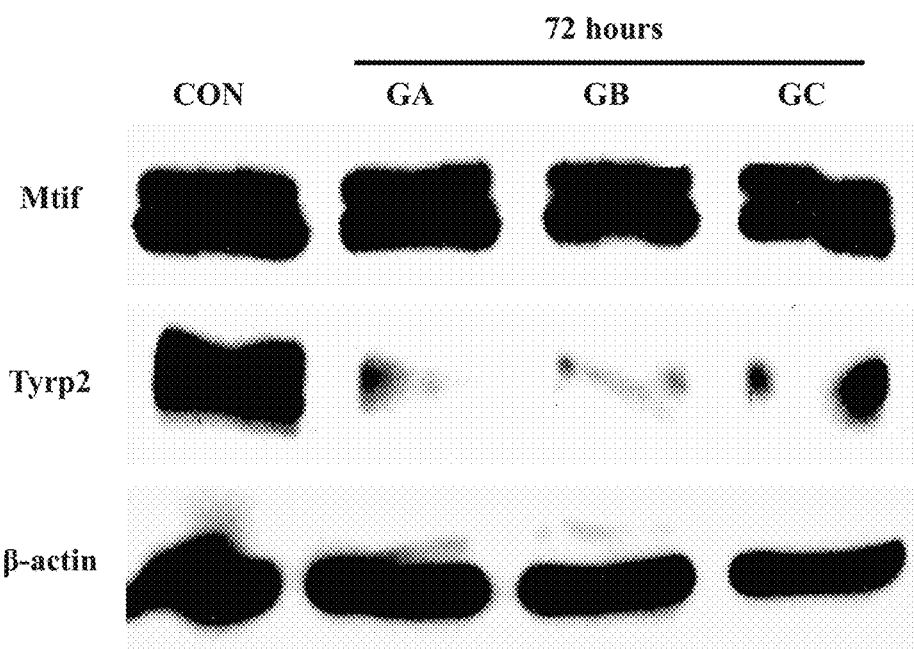
FIG. 7 shows an illustrative micro-photographic representation of the expression of melanogenesis related protein MITF and TRP-2 in ginnalinginnalins-treated B16F0 cells.

Ginnalins did not show down-regulation effects on the protein expression of melanin biosynthesis related enzymes at 5 and 10 µM at 48 hours (data not shown), nor reduce the expressions of these proteins in B16F10 cells that co-incubated with ginnalins for 72 hours. However, in the melanoma cells that were treated with 10 µM of ginnalins A-C for 72 hours, the protein expression of TRP-2 were decrease by 87.9%, 92.0% and 69.5% by ginnalins A-C, respectively (FIG. 6B.). FIG. 7 shows The expression of melanogenesis related protein MITF and TRP-2 in ginnalins-treated B16F0 cells. Cells were treated with or without 10 µm of ginnalins for 72 h and protein expression of MITF and TRP-2 were analyzed by Western blotting.

Figure 8:
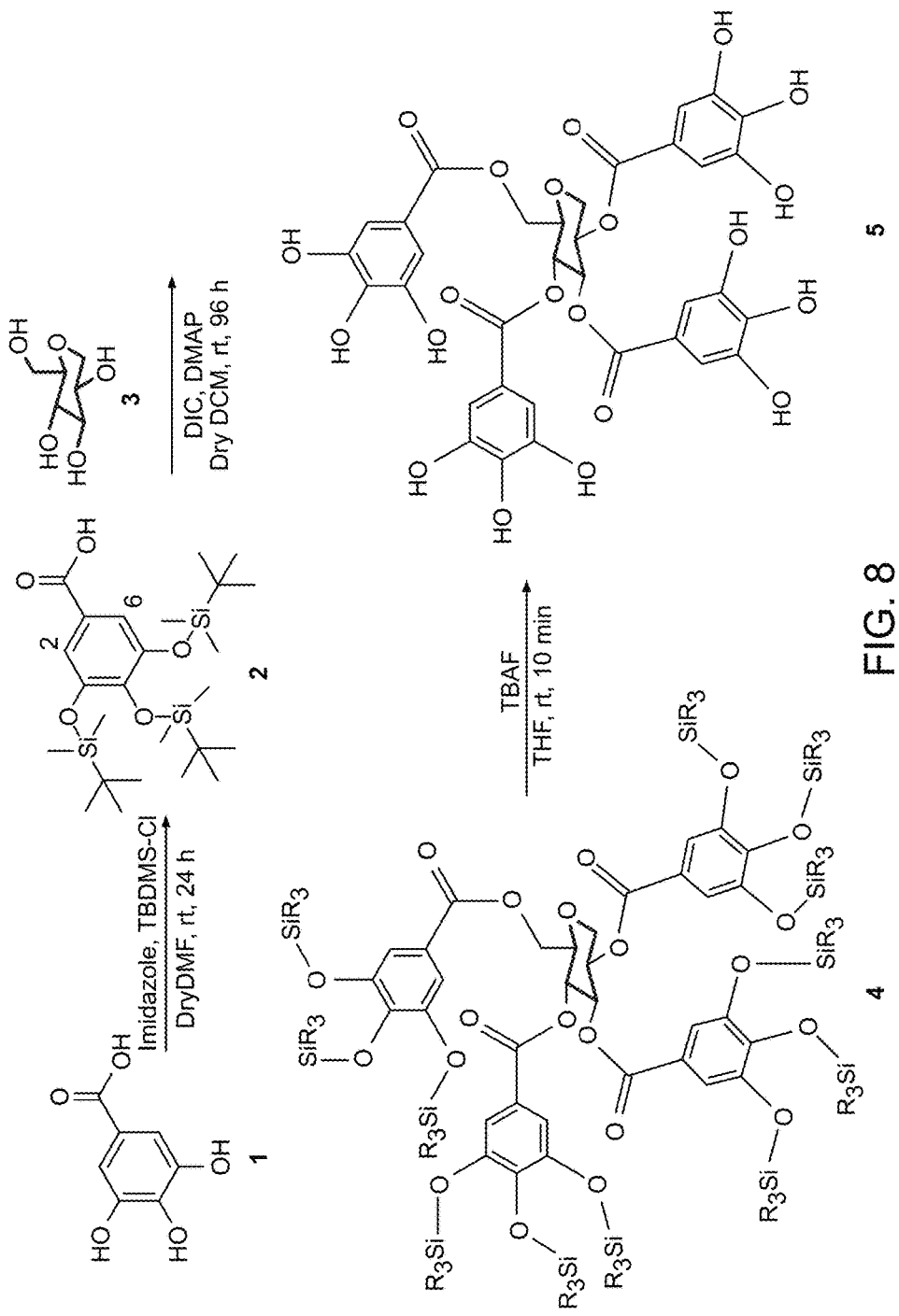
FIG. 8 shows an illustrative view of a method for synthesis of tetragalloylglucitol, named Maplexin J.

Example 4. Synthesis of Maplexin J, a Tetragalloylglucitol with α-Glucosidase Inhibitory Activity The method for the synthesis of the first tetragalloylglucitol, named maplexin J, is shown in FIG. 8. Gallic acid (1, 101 mg, 0.6 mmol) was dissolved in dry N,N-dimethylformamide (DNIF, 2 mL). Imidazole (513 mg, 7.5 mmol) and tert-butyldimethylsilyl chloride (TBDMS, 521 mg, 3.5 mmol) were added to the solution, and the mixture was then stirred at room temperature under nitrogen for 24 h. A white crystalline solid product was formed, which precipitated out of the reaction solution. The trisilyl-protected gallic acid (2) was isolated (244 mg, 82%) from the precipitant using silica gel chromatography with a gradient of hexanes:ethyl acetate starting with hexanes at 100%. The integration of the peaks from the $^1$H NMR spectra of compound 2 confirmed the presence of three substitutions by TBDMS. A hydrolysis reaction of compound 2 with acetic acid (6.9 mg) and $H_2O$ (0.5 mL) in dry tetrahydrofuran (THF, 1 mL) was conducted at room temperature for 24 h, to ensure that there was no protected carboxylic acid. The $^1$H NMR spectra of the hydrolysis product confirmed the retention of the three TBDMS protecting groups as follows: $CH_3OD$ at 500 MHz ($^1$H) δ 0.09 (s, 6H, $(CH_3)_2$—Si), 0.20 (s, 12H, $(CH_3)_4$—Si), 0.88 (s, 18H, $(CH_3)_6$—C), 0.94 (s, 9H, $(CH_3)_3$—C), 7.11 (s, 2H, aromatic protons 2 and 6) (FIG. 8).

Compound 2 (187 mg, 0.4 mmol) and glucitol (3, 10.4 mg, 0.06 mmol) were dissolved in dry dichloromethane (DCM, 2 mL). N,N'-diisopropylcarbodiimide (DIC, 61.4 mg, 0.5 mmol) was added followed by 4-dimethylaminopyridin (DMAP, 74.4 mg, 0.06 mmol). The mixture was stirred at room temperature under nitrogen for 96 h. Water was added to the reaction mixture, and the solution was extracted (×3) using ethyl acetate. The combined organic layer was washed with brine solution, dried over anhydrous sodium sulfate, and concentrated. The crude product was purified using silica gel column chromatography to yield compound 4. The esterification products were isolated using silica gel chromatography with a gradient solvent system of hexanes:ethyl acetate starting with hexanes at 100%. Compound 4 (843 mg, 64.6%) was isolated and its structure was confirmed by HMBC correlations from the three sugar methines and the sugar methylene to the respective carbonyl carbons of the gallic acids.

The deprotection of compound 4 was accomplished in the presence of tetra-n-butylammonium fluoride (TBAF). Compound 4 (50 mg, 0.023 mmol) was dissolved in dry tetrahydrofuran (THF, 2 mL). TBAF (61.1 mg, 0.23 mmol) was added, and the mixture was stirred at room temperature under a nitrogen atmosphere for 10 min. The crude product was purified using reverse-phase HPLC to yield the final product compound 5 (10 mg, 52.3%) which was characterized and assigned the common name of maplexin J.

Figure 9:
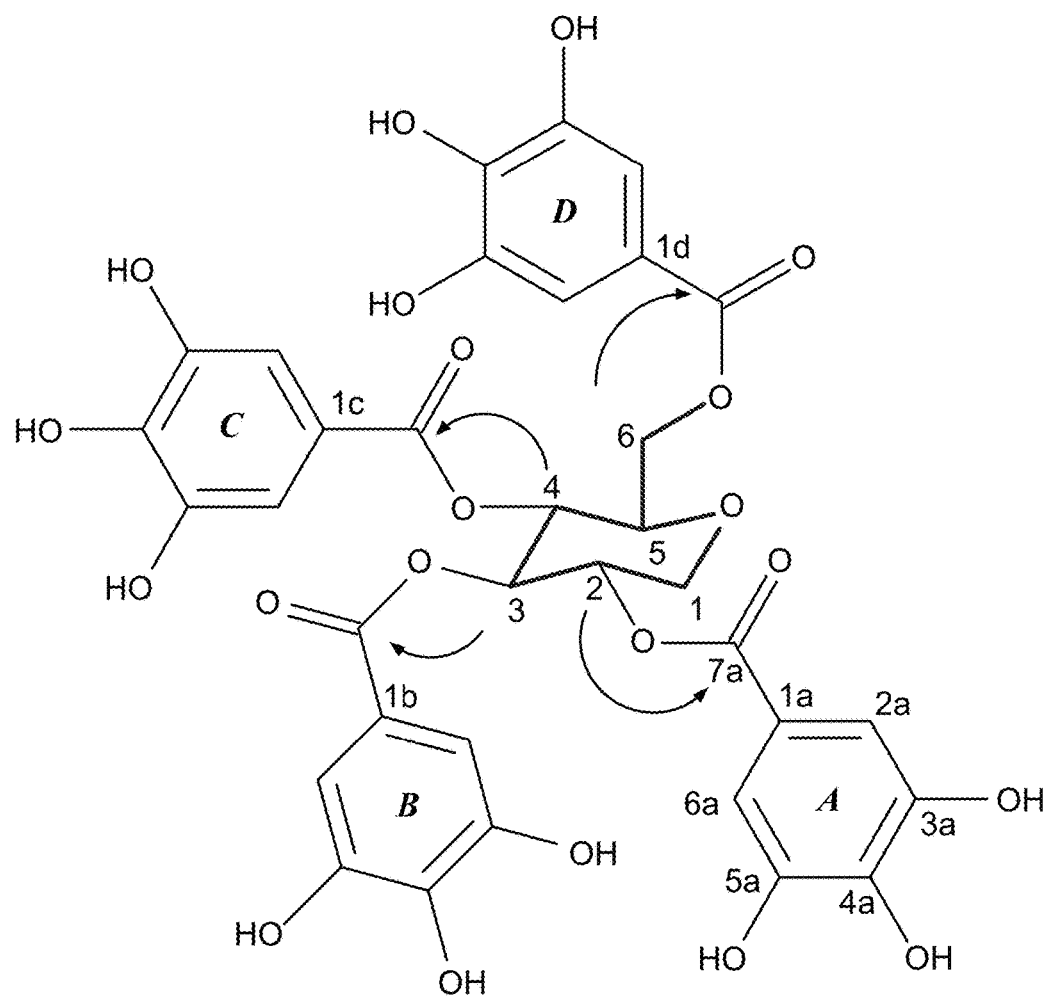
FIG. 9 shows an illustrative view of a further method for the synthesis of Maplexin J.

Detailed analysis of the 1D and 2D NMR spectra data (including $^1$H-$^1$H COSY, HSQC, HMBC) allowed for the establishment of the structure of maplexin J (5) (see FIG. 2 and Table 1). The $^1$H-$^1$H COSY spectra revealed the presence of the glucitol sugar core (from C-1 to C-6), which is shown in bold in FIG. 9. The HMBC spectra data allowed for the connection of the galloyl substituents to the three methines (C2, C3, C4) and methylene (C6) of the glucitol core. Mass spectrometry analysis confirmed the proposed structure ($C_{34}H_{28}O_{21}$; 772.1123): m/z $[M-H]^-$ 771.5421; $[M+Na]^+$ 795.1403.

Maplexin J was evaluated for in vitro α-glucosidase inhibitory activities along with the previously isolated gallotannins, maplexin D and maplexin F, which contain two and three galloyl substituents, respectively. Acarbose, a clinical α-glucosidase inhibitory drug, was used as a positive control. As shown in Table 2, maplexin J that contained four galloylsubstituents was 600- and 5-fold more potent than the disubstituted and trisubstituted maplexins D and F, respectively, and 80 times more potent than the clinical drug, acarbose.

TABLE 2

| Compd. | # of galloyl groups | IC$_{50}$ (μM) |
|---|---|---|
| Maplexin D | 2 | 1221.43 ± 2.52 |
| Maplexin F | 3 | 10.66 ± 0.13 |
| Maplexin J | 4 | 2.63 ± 0.07 |
| Acarbose[b] | | 160.8 ± 18.93 |

α-Glucosidase inhibitory activities of compounds[a]

[a]IC$_{50}$ values are shown as mean ± S.D. from three independent experiments;
[b]Positive control;
n.d. = not detected.

It is described the total synthesis of a potent α-glucosidase inhibitor named maplexin J, which is the first tetragalloylglucitol reported to date. Based on the current study and previous observations, the number of galloyl substituents on the glucitol core is indeed critical for α-glucosidase inhibitory activity. In certain embodiments, the tetragalloylglucitol moiety will serve as a scaffold for the synthesis of structural analogs to improve α-glucosidase inhibitory activity.

The description of the specific embodiments is presented for the purposes of illustration. It is not intended to be exhaustive nor to limit the scope of the invention to the specific forms described herein. Although the invention has been described with reference to several embodiments, it will be understood by one of ordinary skill in the art that various modifications can be made without departing from the spirit and the scope of the invention, as set forth.

What is claimed is:

1. A method of producing a skin whitening extract comprising the compound tetragalloylglucitol, from a part of a maple tree, wherein said method comprises the step of isolating the tetragalloylglucitol from the part of the maple tree.

2. The method as claimed in claim 1, wherein the skin whitening extract further comprises the following compound:

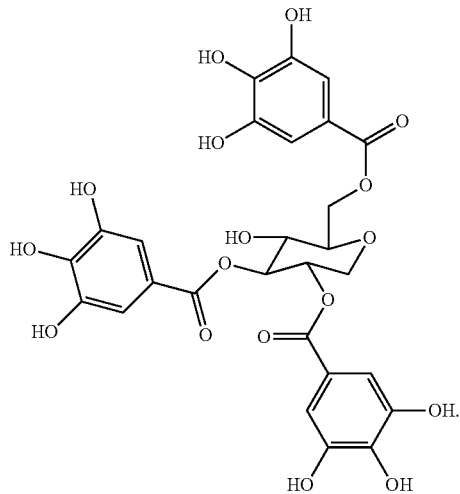 [SMILES: O=C(OCC1OCC(OC(=O)c2cc(O)c(O)c(O)c2)C(OC(=O)c2cc(O)c(O)c(O)c2)C1O)c1cc(O)c(O)c(O)c1]

3. The method as claimed in claim 1, wherein the part of the maple tree comprises the leaves.

* * * * *